(12) United States Patent
Shinbrot et al.

(10) Patent No.: US 10,905,566 B2
(45) Date of Patent: Feb. 2, 2021

(54) PERCUTANEOUS POSTERIOR IMPLANT SLIDE

(71) Applicant: Spineology Inc., St. Paul, MN (US)

(72) Inventors: Adam Shinbrot, Woodbury, MN (US); Dan McPhillips, Ham Lake, MN (US)

(73) Assignee: Spineology Inc., St. Paul, MN (US)

( * ) Notice: Subject to any disclaimer, the term of this patent is extended or adjusted under 35 U.S.C. 154(b) by 71 days.

(21) Appl. No.: 16/268,370

(22) Filed: Feb. 5, 2019

(65) Prior Publication Data
US 2019/0240044 A1  Aug. 8, 2019

Related U.S. Application Data

(60) Provisional application No. 62/626,619, filed on Feb. 5, 2018.

(51) Int. Cl.
*A61F 2/46* (2006.01)

(52) U.S. Cl.
CPC .......... *A61F 2/4611* (2013.01); *A61F 2/4603* (2013.01); *A61F 2002/4615* (2013.01); *A61F 2002/4627* (2013.01)

(58) Field of Classification Search
CPC ........ A61F 2/46; A61F 2/4601; A61F 2/4611; A61B 17/025; A61B 2017/0256; A61B 17/88; A61B 17/885–8858
See application file for complete search history.

(56) References Cited

U.S. PATENT DOCUMENTS

| | | | | | |
|---|---|---|---|---|---|
| 4,545,374 | A | * | 10/1985 | Jacobson | A61B 17/0218 600/210 |
| 5,180,388 | A | * | 1/1993 | DiCarlo | A61B 17/17 606/60 |
| 5,431,658 | A | * | 7/1995 | Moskovich | A61B 17/025 606/90 |
| 5,571,109 | A | * | 11/1996 | Bertagnoli | A61F 2/4611 606/86 A |
| 6,017,342 | A | * | 1/2000 | Rinner | A61B 17/8866 606/57 |
| 6,224,599 | B1 | * | 5/2001 | Baynham | A61B 17/025 606/79 |
| 6,520,967 | B1 | * | 2/2003 | Cauthen | A61B 17/1757 600/219 |
| 7,118,580 | B1 | * | 10/2006 | Beyersdorff | A61F 2/4425 606/99 |
| 8,016,829 | B2 | * | 9/2011 | Mahoney | A61F 2/447 606/86 A |
| RE43,317 | E | * | 4/2012 | Fraser | A61F 2/4611 606/99 |
| 8,328,815 | B2 | * | 12/2012 | Farr | A61B 17/025 606/86 A |

(Continued)

*Primary Examiner* — Eduardo C Robert
*Assistant Examiner* — Michelle C Eckman
(74) *Attorney, Agent, or Firm* — Skaar Ulbrich Macari, P.A.

(57) ABSTRACT

An implant insertion instrument provides a guide through tissue (skin, fascia, musculature) and into a vertebral space after a discectomy. The instrument slides onto a guide wire and defines a path for the implant to be delivered to the vertebral space. The guide expands laterally as required to accommodate the implant as the implant slides through a channel defined in the guide, which allows distraction of the vertebral bodies while maintaining a small incision in the patient.

12 Claims, 4 Drawing Sheets

(56) References Cited

U.S. PATENT DOCUMENTS

| | | | | |
|---|---|---|---|---|
| 8,343,163 B1* | 1/2013 | Arambula | | A61F 2/4611 606/99 |
| 8,377,072 B2* | 2/2013 | Stad | | A61F 2/4611 606/99 |
| 8,419,744 B2* | 4/2013 | Petit | | A61B 34/75 606/99 |
| 8,435,295 B2* | 5/2013 | Williams | | A61F 2/442 623/17.11 |
| 8,500,749 B2* | 8/2013 | Lee | | A61F 2/4611 606/86 A |
| 8,840,621 B2* | 9/2014 | Farr | | A61B 17/025 606/99 |
| 8,840,622 B1* | 9/2014 | Vellido | | A61F 2/4611 606/99 |
| 9,033,993 B2* | 5/2015 | Bae | | A61F 2/447 606/99 |
| RE45,639 E * | 8/2015 | Fraser | | A61F 2/4611 |
| 9,259,213 B1* | 2/2016 | O'Hara | | A61F 2/4611 |
| 9,351,845 B1* | 5/2016 | Pimenta | | A61B 17/3211 |
| 9,545,283 B2* | 1/2017 | Sack | | A61B 17/885 |
| RE46,410 E * | 5/2017 | Fraser | | A61F 2/4611 |
| 9,867,605 B2* | 1/2018 | Adams | | A61B 17/0218 |
| 10,667,915 B2* | 6/2020 | Trischler | | A61F 2/28 |
| 2001/0010001 A1* | 7/2001 | Michelson | | A61F 2/4611 606/99 |
| 2002/0045904 A1* | 4/2002 | Fuss | | A61F 2/4611 606/99 |
| 2002/0116009 A1* | 8/2002 | Fraser | | A61F 2/4611 606/99 |
| 2002/0123753 A1* | 9/2002 | Michelson | | A61B 17/1757 606/90 |
| 2003/0032962 A1* | 2/2003 | McGahan | | A61F 2/4611 606/80 |
| 2003/0055434 A1* | 3/2003 | O'Neil | | A61F 2/4611 606/100 |
| 2003/0149438 A1* | 8/2003 | Nichols | | A61F 2/4611 606/99 |
| 2003/0199874 A1* | 10/2003 | Michelson | | A61B 17/1757 606/86 A |
| 2003/0229355 A1* | 12/2003 | Keller | | A61F 2/4611 606/99 |
| 2004/0002758 A1* | 1/2004 | Landry | | A61F 2/447 623/17.11 |
| 2004/0059261 A1* | 3/2004 | Grinberg | | A61B 90/06 600/587 |
| 2004/0059337 A1* | 3/2004 | Hanson | | A61F 2/4611 606/79 |
| 2004/0082958 A1* | 4/2004 | Michelson | | A61F 2/4611 606/90 |
| 2004/0117019 A1* | 6/2004 | Trieu | | A61F 2/441 623/17.11 |
| 2004/0143331 A1* | 7/2004 | Errico | | A61F 2/4425 623/17.14 |
| 2004/0199168 A1* | 10/2004 | Bertagnoli | | A61F 2/4611 606/99 |
| 2004/0225295 A1* | 11/2004 | Zubok | | A61F 2/4425 606/90 |
| 2004/0267276 A1* | 12/2004 | Camino | | A61F 2/08 606/99 |
| 2005/0021042 A1* | 1/2005 | Marnay | | A61F 2/4611 606/99 |
| 2005/0027300 A1* | 2/2005 | Hawkins | | A61B 17/1659 606/86 R |
| 2005/0075643 A1* | 4/2005 | Schwab | | A61F 2/4611 606/90 |
| 2005/0119665 A1* | 6/2005 | Keller | | A61F 2/4611 606/99 |
| 2005/0165408 A1* | 7/2005 | Puno | | A61F 2/4611 606/99 |
| 2005/0215862 A1* | 9/2005 | Larson | | A61B 17/02 600/201 |
| 2006/0069315 A1* | 3/2006 | Miles | | A61B 5/1104 600/219 |
| 2006/0089656 A1* | 4/2006 | Allard | | A61F 2/4611 606/99 |
| 2006/0111728 A1* | 5/2006 | Abdou | | A61F 2/4611 606/86 R |
| 2006/0195097 A1* | 8/2006 | Evans | | A61F 2/4611 606/86 A |
| 2006/0217754 A1* | 9/2006 | Boehm, Jr. | | A61B 17/025 606/191 |
| 2006/0241641 A1* | 10/2006 | Albans | | A61B 17/0218 606/90 |
| 2007/0073405 A1* | 3/2007 | Verhulst | | A61F 2/4425 623/17.15 |
| 2007/0100347 A1* | 5/2007 | Stad | | A61F 2/4611 606/90 |
| 2007/0123903 A1* | 5/2007 | Raymond | | A61F 2/4611 606/99 |
| 2007/0123904 A1* | 5/2007 | Stad | | A61F 2/4611 606/99 |
| 2007/0191857 A1* | 8/2007 | Allard | | A61F 2/4611 606/90 |
| 2007/0209222 A1* | 9/2007 | Fischer | | A61F 2/4684 33/512 |
| 2008/0077156 A1* | 3/2008 | Emstad | | A61B 17/025 606/105 |
| 2008/0177275 A1* | 7/2008 | Wing | | A61F 2/4611 606/99 |
| 2008/0221586 A1* | 9/2008 | Garcia-Bengochea | | A61B 17/34 606/108 |
| 2008/0242940 A1* | 10/2008 | Stefanchik | | A61B 17/22031 600/235 |
| 2008/0269764 A1* | 10/2008 | Blain | | A61B 17/025 606/99 |
| 2008/0287995 A1* | 11/2008 | Gauthier | | A61B 17/0206 606/246 |
| 2009/0005784 A1* | 1/2009 | Blain | | A61B 17/025 606/90 |
| 2009/0012527 A1* | 1/2009 | Mignucci | | A61F 2/4611 606/99 |
| 2009/0030422 A1* | 1/2009 | Parsons | | A61F 2/4611 606/99 |
| 2009/0048604 A1* | 2/2009 | Milz | | A61B 17/885 606/99 |
| 2009/0062619 A1* | 3/2009 | Bjork | | A61B 17/025 600/219 |
| 2009/0177205 A1* | 7/2009 | McCormack | | A61B 17/1659 606/90 |
| 2009/0234362 A1* | 9/2009 | Blain | | A61F 2/4455 606/90 |
| 2009/0306672 A1* | 12/2009 | Reindel | | A61F 2/4611 606/90 |
| 2010/0023013 A1* | 1/2010 | Flickinger | | A61F 2/4611 606/79 |
| 2010/0076502 A1* | 3/2010 | Guyer | | A61F 2/4611 606/86 R |
| 2010/0076557 A1* | 3/2010 | Miller | | A61F 2/4465 623/17.11 |
| 2010/0114183 A1* | 5/2010 | Wassinger | | A61F 2/4611 606/86 A |
| 2010/0160983 A1* | 6/2010 | Runco | | A61F 2/4611 606/86 A |
| 2010/0210917 A1* | 8/2010 | Fallin | | A61B 17/3421 600/225 |
| 2010/0262199 A1* | 10/2010 | Wallenstein | | A61F 2/4611 606/86 A |
| 2011/0034777 A1* | 2/2011 | Ames | | A61B 17/025 600/206 |
| 2011/0071634 A1* | 3/2011 | Jiang | | A61B 17/025 623/17.11 |
| 2011/0112586 A1* | 5/2011 | Guyer | | A61F 2/4611 606/86 A |
| 2011/0166611 A1* | 7/2011 | Stinson | | A61F 2/4611 606/86 A |

(56) References Cited

U.S. PATENT DOCUMENTS

| | | | |
|---|---|---|---|
| 2012/0022575 A1* | 1/2012 | Mire | A61B 5/4893 606/198 |
| 2012/0253412 A1* | 10/2012 | Lee | A61B 17/025 606/86 A |
| 2012/0310048 A1* | 12/2012 | Siegal | A61B 17/025 600/206 |
| 2013/0110113 A1* | 5/2013 | Glazer | A61B 17/025 606/90 |
| 2013/0178862 A1* | 7/2013 | Garcia-Bengochea | A61F 2/4611 606/99 |
| 2013/0226244 A1* | 8/2013 | Davenport | A61F 2/4611 606/279 |
| 2013/0226253 A1* | 8/2013 | Davenport | A61F 2/4465 606/86 A |
| 2013/0289354 A1* | 10/2013 | Ainsworth | A61B 17/0206 600/204 |
| 2014/0066941 A1* | 3/2014 | Mignucci | A61F 2/3094 606/99 |
| 2014/0114140 A1* | 4/2014 | Ellman | A61B 17/0206 600/249 |
| 2014/0128682 A1* | 5/2014 | Loebl | A61B 17/025 600/206 |
| 2014/0330384 A1* | 11/2014 | Puno | A61B 17/1757 623/17.16 |
| 2014/0343559 A1* | 11/2014 | Flickinger | A61F 2/4611 606/90 |
| 2015/0045895 A1* | 2/2015 | Laurence | A61F 2/4465 623/17.16 |
| 2015/0066039 A1* | 3/2015 | Siegal | A61B 17/025 606/90 |
| 2015/0073421 A1* | 3/2015 | Siegal | A61B 17/7055 606/90 |
| 2015/0080973 A1* | 3/2015 | Eastlack | A61B 17/025 606/86 A |
| 2016/0022429 A1* | 1/2016 | Greenhalgh | A61F 2/442 623/17.16 |
| 2016/0058578 A1* | 3/2016 | Lauryssen | A61B 17/3439 606/86 A |
| 2016/0100952 A1* | 4/2016 | Moskowitz | A61F 2/4611 623/17.16 |
| 2016/0120663 A1* | 5/2016 | Theofilos | A61F 2/4465 606/99 |
| 2016/0220389 A1* | 8/2016 | Dinville | A61F 2/442 |
| 2016/0270930 A1* | 9/2016 | Siegal | A61F 2/447 |
| 2016/0287236 A1* | 10/2016 | Garcia-Bengochea | A61B 17/0218 |
| 2016/0345951 A1* | 12/2016 | Reimels | A61B 17/025 |
| 2017/0071639 A1* | 3/2017 | Glazer | A61B 17/7077 |
| 2017/0086988 A1* | 3/2017 | Kim | A61F 2/4465 |
| 2017/0209155 A1* | 7/2017 | Peteresen | A61B 17/1671 |
| 2017/0245997 A1* | 8/2017 | Trischler | A61F 2/30771 |
| 2018/0092758 A1* | 4/2018 | Garcia-Bengochea | A61F 2/4611 |
| 2018/0193158 A1* | 7/2018 | Suddaby | A61F 2/4455 |
| 2018/0303631 A1* | 10/2018 | Phan | A61F 2/4601 |
| 2018/0344481 A1* | 12/2018 | Garcia-Bengochea | A61B 17/025 |
| 2018/0368861 A1* | 12/2018 | Garcia-Bengochea | A61B 17/1757 |
| 2019/0021874 A1* | 1/2019 | Pimenta | A61F 2/4611 |
| 2019/0091038 A1* | 3/2019 | Boylan | A61F 2/4611 |
| 2019/0240044 A1* | 8/2019 | Shinbrot | A61F 2/4611 |
| 2019/0307439 A1* | 10/2019 | Chhit | A61B 17/0206 |
| 2019/0380691 A1* | 12/2019 | Sandhu | A61B 17/025 |
| 2020/0015985 A1* | 1/2020 | Rogers | A61F 2/4611 |

\* cited by examiner

PERCUTANEOUS POSTERIOR IMPLANT SLIDE

PRIORITY

This application claims the benefit of U.S. Provisional Application Ser. No. 62/626,619, filed on Feb. 5, 2018, which is hereby incorporated herein by reference in its entirety.

FIELD

The present invention generally relates to surgical tools. More particularly, the present invention relates to an implant insertion tool or instrument for delivering an implant to a vertebral space.

BACKGROUND

Implants for vertebral surgical procedures are commonly inserted into the vertebral space after a series of dilators, of increasing size, are used to create the path for the implant to travel through the patient's tissues. The larger the dilator, the more impingement and possible tissue damage that can occur. Thus, there is a continuing need to provide insertion tools and methods that minimize impingement and possible tissue damage while providing for insertion of an implant.

SUMMARY

The disclosure includes an implant insertion tool or instrument that provides a guide through tissue (skin, fascia, musculature) and into a vertebral space after a discectomy. The instrument slides onto a guide wire and defines a path for the implant to be delivered to the vertebral space. The guide expands as required to accommodate the implant as the implant slides through the guide, which allows distraction of the vertebral bodies while maintaining a small incision in the patient.

An implant insertion system according to one example embodiment can include an insertion instrument; and a guide instrument that mates with the insertion instrument. The guide instrument can comprise an elongated body that defines a center channel extending longitudinally through the body and a flexible slide that encloses an open side of the center channel.

The flexible slide can include a tongue extending from an edge thereof. The body can include a groove defined in a sidewall thereof that extends along the channel. The tongue can be located such that it can engage the groove to permit movement of the slide in a direction perpendicular to a longitudinal axis of the channel while maintaining a longitudinal location with respect to the slide.

The insertion instrument can comprise a handle defined on a proximal end thereof.

A distal end of the insertion instrument can be tapered and shaped such that the distal end facilitates movement through a patient's tissues.

An implant inserter can be mated with a proximal end of the guide instrument.

An implant guide instrument according to one example embodiment can comprise an elongated body that defines a center channel extending longitudinally through the body and a flexible slide that encloses an open side of the center channel. The flexible slide can include a tongue extending from an edge thereof. The body can include a groove defined in a sidewall thereof that extends along the channel. The tongue can be located such that it can engage the groove to permit movement of the slide in a direction perpendicular to a longitudinal axis of the channel while maintaining a longitudinal location with respect to the slide.

An example embodiment of a method of inserting a spinal implant through a patient's tissues to deliver the implant to a vertebral space is also provided. The method can include mating an insertion instrument with a guide instrument. A distal end of the insertion instrument can be tapered and shaped to facilitate movement through the patient's tissues. The guide instrument can define a channel extending longitudinally through the guide instrument. The guide instrument can be inserted through the patient's tissues so that a distal end of the guide instrument can communicate with vertebral space. The insertion instrument can be removed from the guide instrument while leaving the guide instrument inserted through the patient's tissues. An implant inserter can be mated with a proximal end of the guide instrument. The implant can be moved through the guide instrument towards the distal end of the guide instrument. A slide can be provided to the channel to enclose an open side of the channel. While the implant is moving through the guide instrument, the implant can cause the slide disposed in the channel to flex in a direction perpendicular to an axis of the channel.

A longitudinal location of the slide with respect to the channel can be maintained via a tongue of the slide engaging a groove defined in the channel.

The detailed technology and preferred embodiments implemented for the subject invention are described in the following paragraphs accompanying the appended drawings for people skilled in this field to well appreciate the features of the claimed invention. It is understood that the features mentioned hereinbefore and those to be commented on hereinafter may be used not only in the specified combinations, but also in other combinations or in isolation, without departing from the scope of the present invention.

Figure 1:
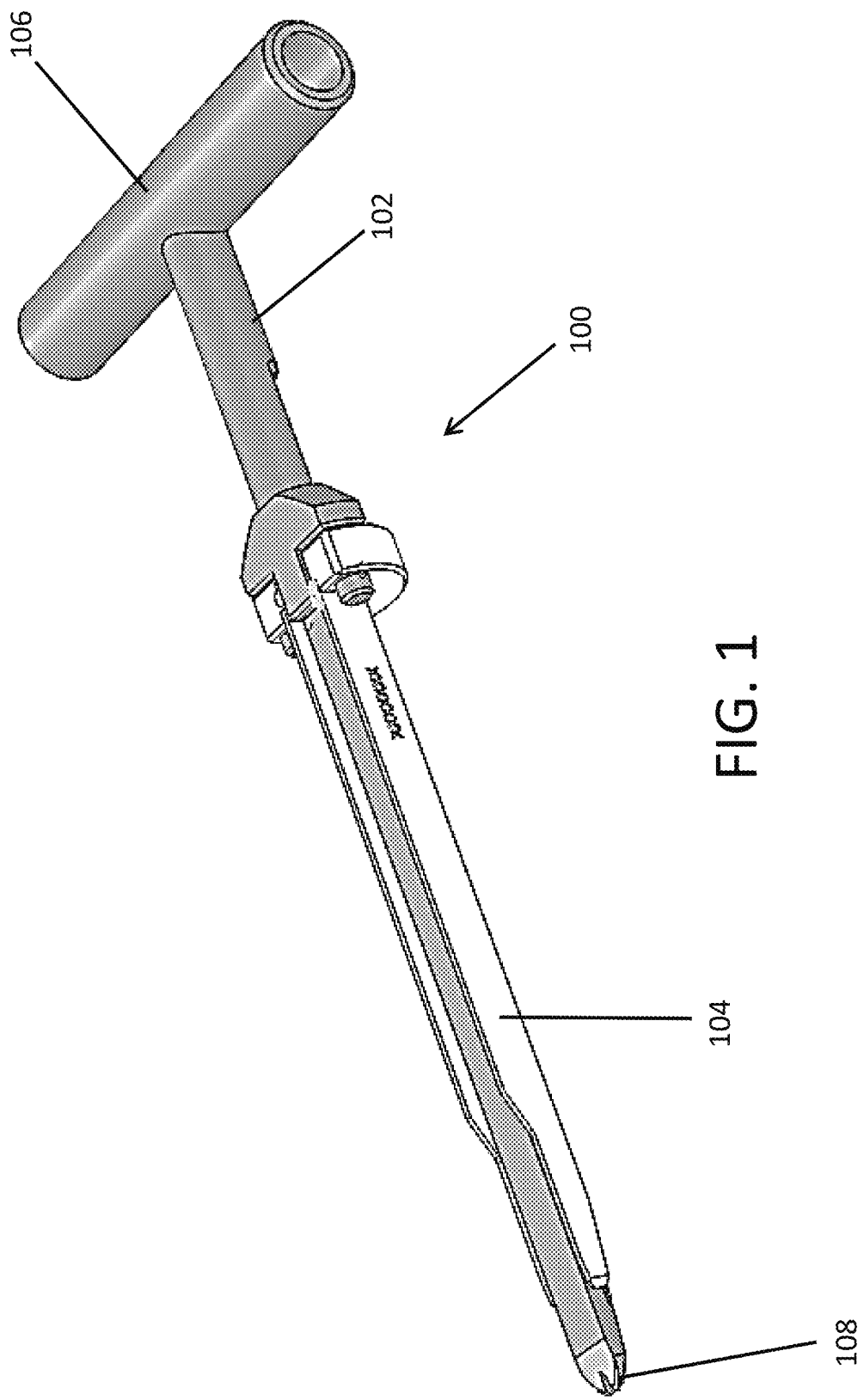
FIG. 1 is a perspective view of an implant insertion system in accordance with certain embodiments.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the spirit and scope of the invention as defined by the appended claims.

DETAILED DESCRIPTION

In the following descriptions, the present invention will be explained with reference to example embodiments thereof. However, these embodiments are not intended to limit the present invention to any specific example, embodiment, environment, applications or particular implementations described in these embodiments. Therefore, description of these embodiments is only for purpose of illustration rather than to limit the present invention. It should be appreciated that, in the following embodiments and the attached drawings, elements unrelated to the present invention are omitted from depiction; and dimensional relationships among individual elements in the attached drawings are illustrated only for ease of understanding, but not to limit the actual scale.

Referring to FIGS. 1-4, the implant insertion system 100 generally comprises an insertion instrument 102 and a guide instrument 104.

In FIG. 1, the insertion instrument 102 is shown fully engaged with the guide instrument 104. This allows the combined system or assembly 100 to be inserted through the patient's tissue (skin, fascia, musculature) until the distal end thereof communicates with the patient's vertebral space after a discectomy has been performed on the patient.

A handle 106 is defined on a proximal end of the insertion instrument 102 to allow the surgeon to confidently manipulate the combined assembly 100. The distal end 108 of the insertion instrument 102 is tapered and shaped to facilitate movement through the patient's tissues.

Figure 2:
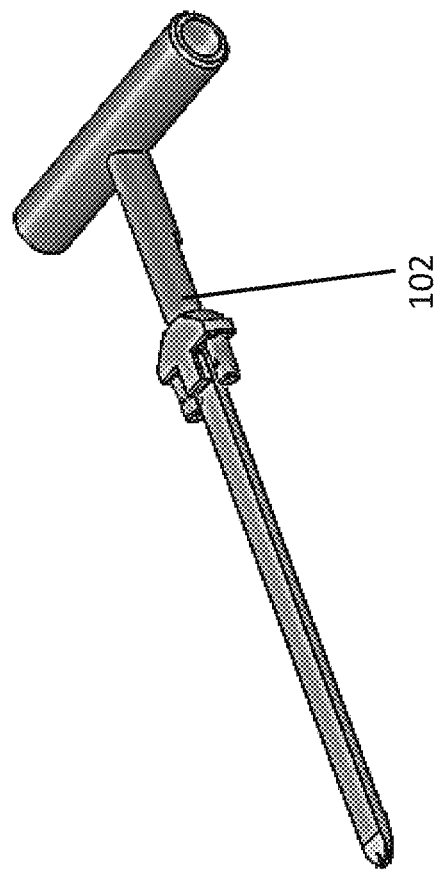
FIG. 2 is a perspective view of the implant insertion system of FIG. 1 with the insertion instrument separated from the guide instrument.
Figure 2:
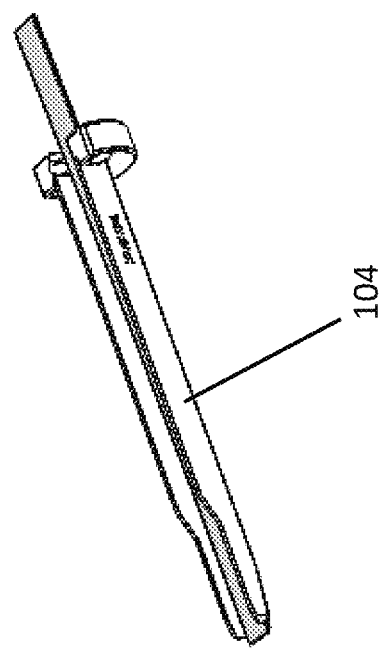

In FIG. 2, the insertion instrument 102 is shown after it has been withdrawn from the guide instrument 104. The guide instrument 104 remains disposed in the patient while the insertion instrument 102 is removed. An implanting path defined through the patient's tissues to the implant delivery site is then ready for the implant and implant inserter.

Figure 3:
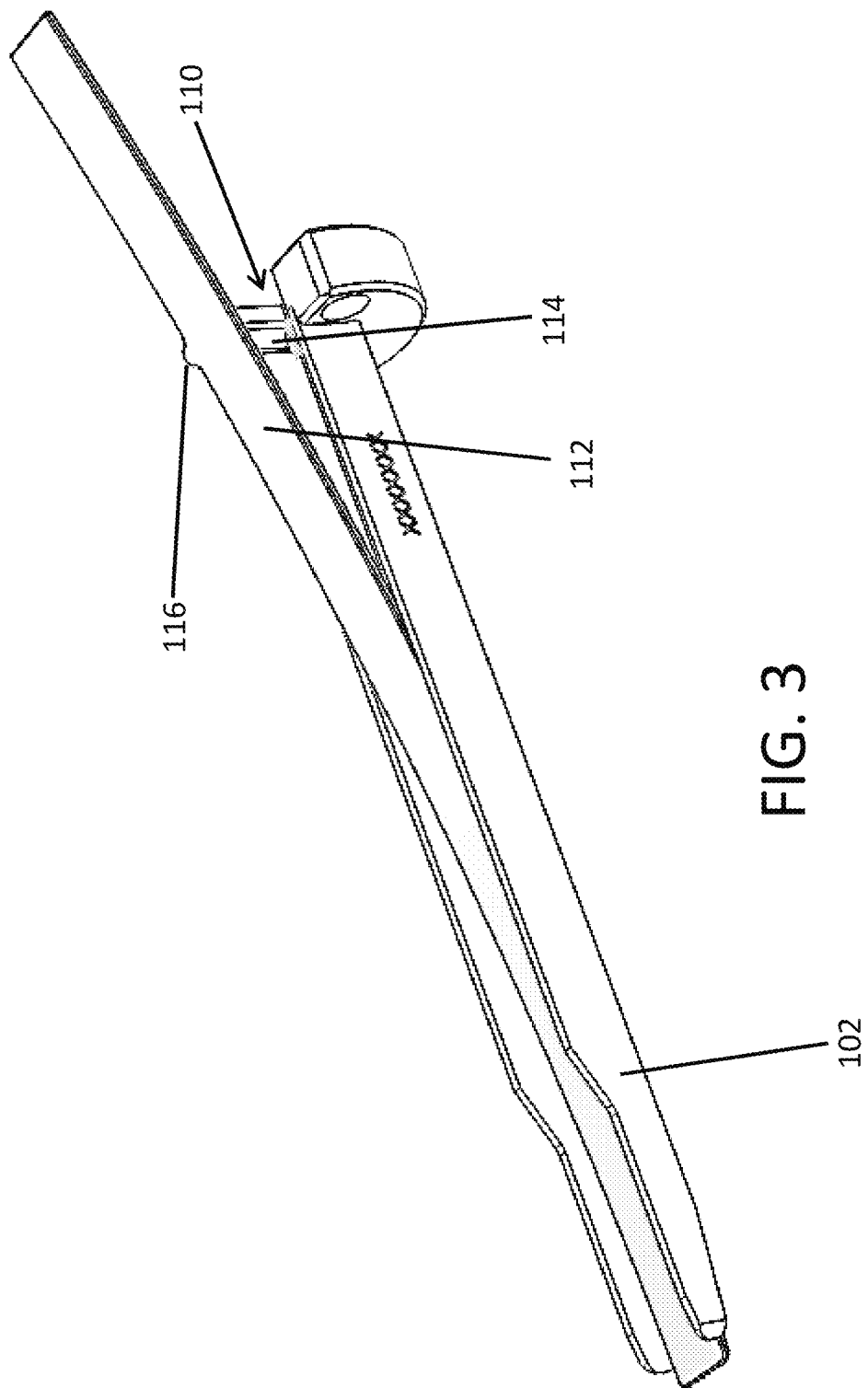
FIG. 3 is a perspective view of the guide instrument of FIGS. 1-2.

FIG. 3 illustrates the guide instrument 104 in greater detail. The guide instrument 104 has an elongated body and defines a center channel 110. The top side of the channel is defined by a movable slide element 112. In this illustration, the proximal end of the slide 112 is lifted upwards from the channel bottom so that the implant can be introduced into the channel 110.

A groove 114 can be defined in a sidewall of the channel 110 so that a tongue 116 of the slide element 112 can engage the groove 114 to permit movement of the slide element in a direction perpendicular to the longitudinal length of the channel 110, but will maintain the longitudinal location of the slide element 112. Thus, the guide instrument 104 provides a four-sided guide path for insertion of the implant. This guide path expands in one direction as required to fit the A-P or lateral dimension of the implant. The guide instrument 104 fits through a small incision and expands as required to pass the implant to the delivery site.

Additionally the guide instrument 104 allows vertebral distraction to occur in conjunction with its lateral expansion.

Figure 4:
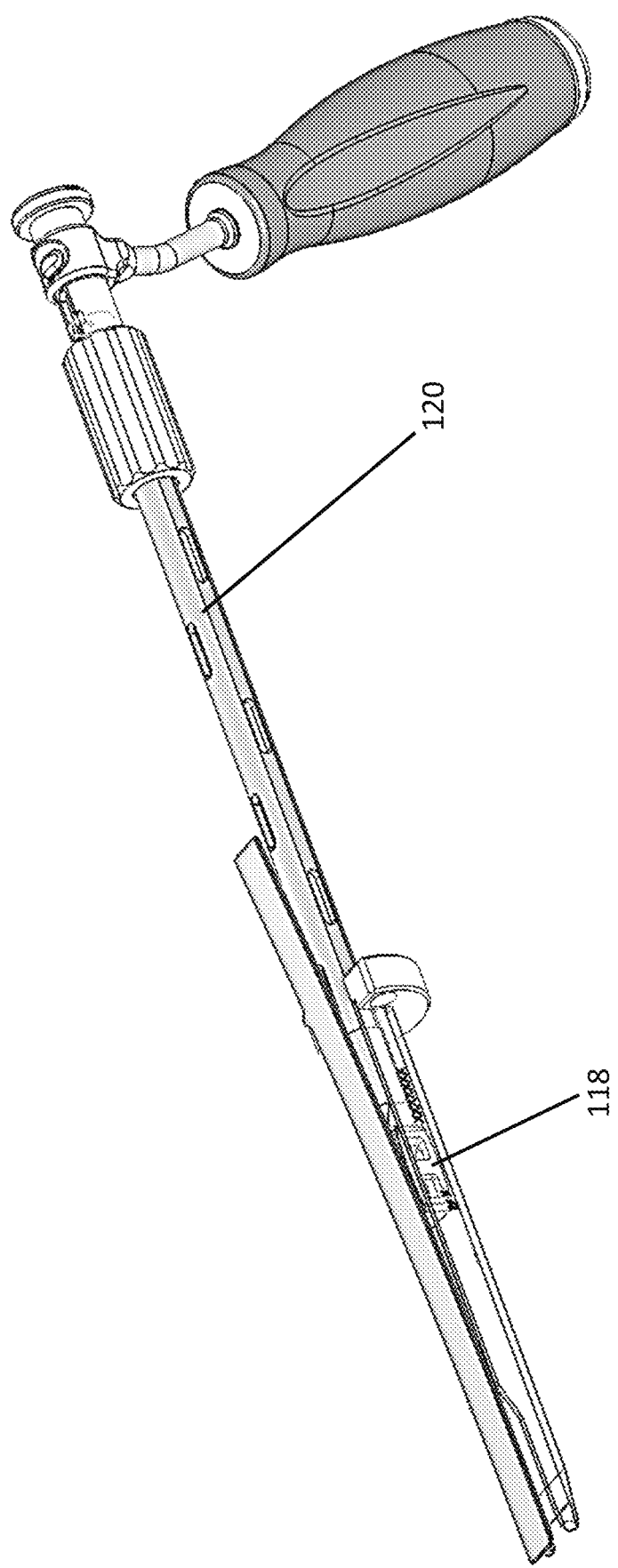
FIG. 4 is a perspective view of the guide instrument of FIGS. 1-3 mated with an instrument inserter instrument and showing an implant passing through the guide instrument.

FIG. 4 illustrates an implant 118 traveling distally through the guide instrument 104. The slide element 112 can be seen flexing laterally to allow the implant 118 to pass through the channel 110 in a distal direction along the longitudinal axis of the guide instrument 104. An implant inserter 120 is mated with the proximal end of the guide instrument 104 and is engaged with the implant 118 in this example.

The present guide instrument 104 and insertion system 100 advantageously minimize tissue impingement and damage potential to the patient's anatomy during an implant delivery procedure.

A variety of implants, and particularly vertebral implants, can be used with the present system and instruments, including cages, spacers, expandable spacers, fillable mesh implants, hybrids of the foregoing, etc.

The present system can be provided in kit form along with the implant itself and an implant inserter. Instructions and other instruments can also be included in the kit. Some or all portions of the kit can be disposable. The kit can also be reusable after suitable sterilization.

The components of the implant insertion system 100 can be formed of suitable surgical metals, non-metals, or a combination thereof.

The present invention may be embodied in other specific forms without departing from the spirit or essential attributes thereof, and it is, therefore, desired that the present embodiment be considered in all respects as illustrative and not restrictive. Those skilled in the art may recognize other equivalents to the specific embodiment described herein which equivalents are intended to be encompassed by the claims attached hereto.

What is claimed is:

1. An implant insertion system, comprising:
an insertion instrument; and
a guide instrument that mates with the insertion instrument,
wherein the guide instrument comprises:
an elongated body that defines a center channel extending longitudinally through the elongated body; and
a flexible slide that encloses an open side of the center channel,
wherein the flexible slide includes a tongue extending from an edge thereof,
wherein the elongated body includes a groove defined in a sidewall thereof that extends along the channel, and
wherein the tongue is located such that it can engage the groove to permit movement of the flexible slide in a direction perpendicular to a longitudinal axis of the channel while maintaining a longitudinal location with respect to the flexible slide.

2. The implant insertion system of claim 1, wherein the insertion instrument comprises a handle defined on a proximal end thereof.

3. The implant insertion system of claim 2, wherein a distal end of the insertion instrument is tapered and shaped such that the distal end facilitates movement through a patient's tissues.

4. The implant insertion system of claim 1, wherein a distal end of the insertion instrument is tapered and shaped such that the distal end facilitates movement through a patient's tissues.

5. The implant insertion system of claim 1, further comprising an implant inserter that can be mated with a proximal end of the guide instrument.

6. A method of inserting a spinal implant through a patient's tissues to deliver the implant to a vertebral space, the method comprising:
mating an insertion instrument with a guide instrument, wherein a distal end of the insertion instrument is tapered and shaped to facilitate movement through the patient's tissues, and wherein the guide instrument defines a channel extending longitudinally through the guide instrument;
inserting the guide instrument through the patient's tissues so that a distal end of the guide instrument can communicate with vertebral space;
removing the insertion instrument from the guide instrument while leaving the guide instrument inserted through the patient's tissues;
mating an implant inserter with a proximal end of the guide instrument;
moving the implant through the guide instrument towards the distal end thereof;
providing a slide to the channel to enclose an open side of the channel; and while the implant is moving through the guide instrument, the implant flexing a slide disposed in the channel in a direction perpendicular to an axis of the channel.

7. The method of claim 6, further comprising maintaining a longitudinal location of the slide with respect to the channel via a tongue of the slide engaging a groove defined in the channel.

8. An implant insertion system, comprising:
an insertion instrument;
a guide instrument that mates with the insertion instrument,
an implant inserter that can be mated with a proximal end of the guide instrument,
wherein the guide instrument comprises:
   an elongated body that defines a center channel extending longitudinally through the elongated body; and
   a flexible slide that encloses an open side of the center channel.

9. The implant insertion system of claim 8, wherein
the flexible slide includes a tongue extending from an edge thereof,
the elongated body includes a groove defined in a sidewall thereof that extends along the channel, and
the tongue is located such that it can engage the groove to permit movement of the flexible slide in a direction perpendicular to a longitudinal axis of the channel while maintaining a longitudinal location with respect to the flexible slide.

10. The implant insertion system of claim 8, wherein the insertion instrument comprises a handle defined on a proximal end thereof.

11. The implant insertion system of claim 10, wherein a distal end of the insertion instrument is tapered and shaped such that the distal end facilitates movement through a patient's tissues.

12. The implant insertion system of claim 8, wherein a distal end of the insertion instrument is tapered and shaped such that the distal end facilitates movement through a patient's tissues.

* * * * *